United States Patent
Deacon et al.

(10) Patent No.: US 6,267,768 B1
(45) Date of Patent: *Jul. 31, 2001

(54) LENS PROTECTOR FOR INTRAOCULAR LENS INSERTER

(75) Inventors: Jim Deacon, Goleta; Thomas M. McNicholas, Laguna Niguel, both of CA (US)

(73) Assignee: Allergan, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/273,367

(22) Filed: Mar. 22, 1999

Related U.S. Application Data

(62) Division of application No. 09/023,028, filed on Feb. 12, 1998, now Pat. No. 5,921,989.

(51) Int. Cl.⁷ ........................................................ A61F 9/00
(52) U.S. Cl. .................................................................. 606/107
(58) Field of Search ........................ 606/107, 108, 606/106

(56) References Cited

U.S. PATENT DOCUMENTS

| | | | |
|---|---|---|---|
| 2,730,101 | * | 1/1956 | Hoffman ............................ 606/108 |
| 3,888,258 | * | 6/1975 | Akiyama ............................ 606/108 |
| 4,681,102 | | 7/1987 | Bartell . |
| 4,836,202 | * | 6/1989 | Krasner ............................ 606/107 |
| 4,862,885 | | 9/1989 | Cumming . |
| 4,880,000 | | 11/1989 | Holmes et al. . |
| 4,919,130 | * | 4/1990 | Stoy et al. ........................ 606/107 |
| 4,976,716 | | 12/1990 | Cumming . |
| 5,066,297 | | 11/1991 | Cumming . |
| 5,123,905 | * | 6/1992 | Kelman ............................ 606/107 |
| 5,494,484 | | 2/1996 | Feingold . |
| 5,496,328 | * | 3/1996 | Nakajima et al. ............... 606/107 |
| 5,562,699 | | 10/1996 | Heimberger et al. . |
| 5,582,613 | * | 12/1996 | Brady et al. ..................... 606/107 |
| 5,582,614 | | 12/1996 | Feingold . |
| 5,643,276 | * | 7/1997 | Zaleski ............................ 606/107 |
| 5,681,323 | * | 10/1997 | Arick ............................... 606/108 |
| 5,735,858 | | 4/1998 | Makker et al. . |
| 5,910,144 | * | 1/1999 | Hayashi ........................... 606/108 |

FOREIGN PATENT DOCUMENTS

| | | |
|---|---|---|
| 9206735 | 4/1992 | (WO) . |
| 9513022 | 5/1995 | (WO) . |
| 9637152 | 11/1996 | (WO) . |
| 9726844 | 7/1997 | (WO) . |

* cited by examiner

*Primary Examiner*—Todd E. Manahan
*Assistant Examiner*—Eduardo C. Robert
(74) *Attorney, Agent, or Firm*—Stout, Uxa, Buyan & Mullins; Frank J. Uxa

(57) ABSTRACT

An apparatus for inserting an intraocular lens through an incision into an eye includes a tube defining a hollow passage, an injector rod longitudinally moveable within the hollow passage and a force transfer assembly coupled to the injector rod. The injector rod has a distal portion adapted to contact the intraocular lens within the hollow passage of the tube to urge the intraocular lens distally through the hollow passage. The force transfer assembly is adapted to transfer sufficient force to the injector rod to effect the longitudinal movement of the injector rod and is further adapted to prevent the transfer of sufficient force to the injector rod to effect the longitudinal movement of the injector rod in response to an increased amount of force being applied to the force transfer assembly.

20 Claims, 3 Drawing Sheets

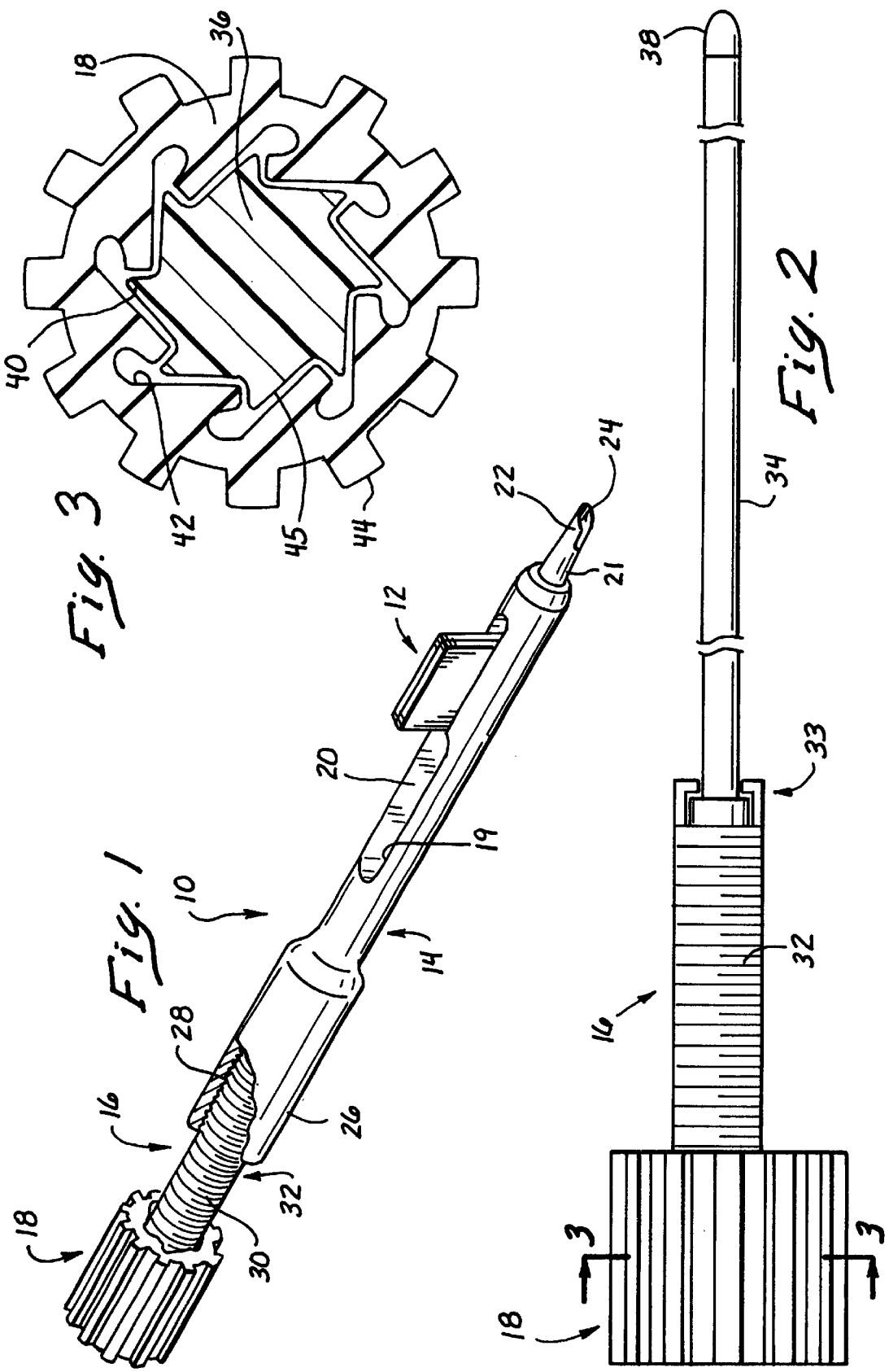

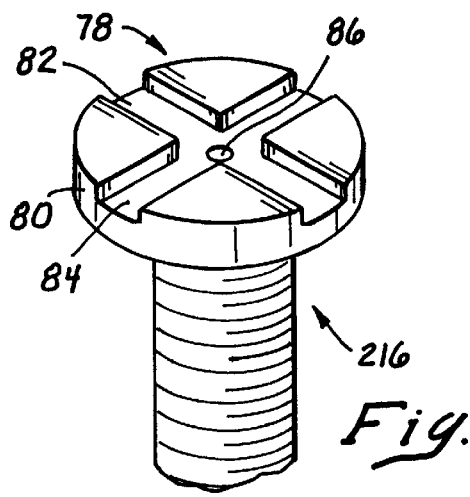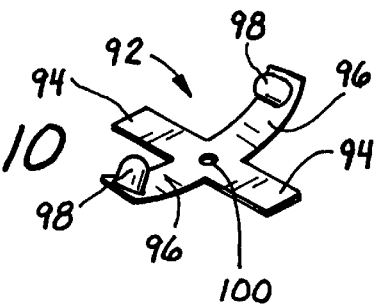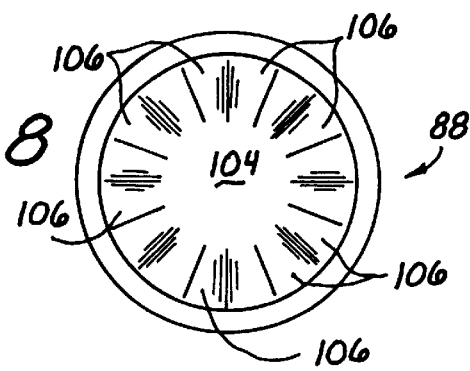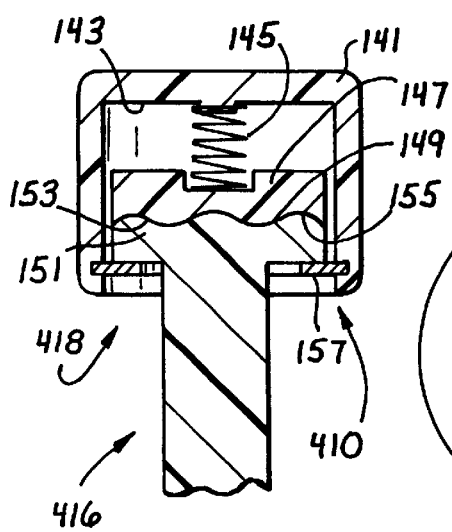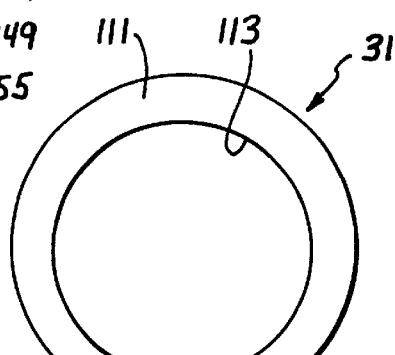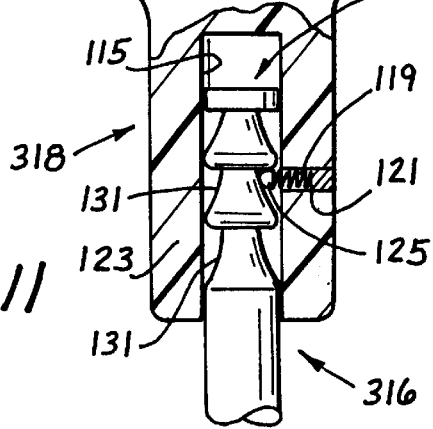

LENS PROTECTOR FOR INTRAOCULAR LENS INSERTER

This application is a division of application Ser. No. 09/023,028 filed Feb. 12, 1998, U.S. Pat. No. 5,921,489 the disclosure of which is incorporated in its entirety herein by reference.

FIELD OF THE INVENTION

The present invention relates generally to the field of intraocular lenses (IOLs), more particularly to mechanical devices for inserting IOLs in patients' eyes, and still more particularly to mechanical devices having force-limiting mechanisms incorporated into the advancing mechanisms of these devices.

BACKGROUND OF THE INVENTION

A leading cause of partial or total blindness in humans, especially the elderly, is cataracts—which is defined as a condition of opacity of the eye's naturally transparent lens through which light entering the eye is focused to the fovis centralis of the retina to form images of viewed objects. As cataracts progress, opacity of the afflicted lens increases and less and less light is transmitted through the lens to the retina, thereby causing an individual's sight to deteriorate, in worst case, to complete blindness.

Because opacity of a natural ocular lens cannot currently—and probably not in the foreseeable future—be reversed or eliminated, the only "cure", previously and still available, for severe cataracts is surgical removal of the afflicted natural lens in its entirety.

After removal of the natural lens, the patient's vision, until relatively recently, was restored to a greater or lesser extent by fitting him or her with spectacles which provided the light focusing previously provided by the natural lens before the formation of cataracts. Spectacles having very thick, heavy and unattractive "coke-bottle" lenses were typically needed to restore reasonably normal vision to the patient.

As a more satisfactory alternative to the thick spectacles used after natural lens removal, artificial lenses, called intraocular lenses, have been developed over the last few decades and are now commonly used as in situ replacements for removed natural lenses. This superior means of restoring a patient's vision after cataract surgery arose after the serendipitous discovery by Dr. Peter Ridley during World War II that embedded fragments of perspex (PLEXIGLAS®) from shattered wind screens of fighter aircraft were tolerated for long periods of time in the eyes of British pilots. This discovery by Dr. Ridley of the biocompatibility of perspex, a polymethylmethacrylate (PMMA) plastic, gave rise to the surgical practice of implanting artificial lenses inside the eye.

Until the early 1980's, natural lenses, which are typically about 8 (eight) mm in diameter, were surgically removed in one piece from the patient's eyes through ocular incisions that were about the same length as the diameter of the removed lenses. Replacement IOLs are typically implanted in the same surgical procedure in which the natural lens had been removed through the same ocular incision made to remove the natural lens. Consequently, rigid IOLs, typically constructed from PMMA, and having about a six mm optic, could be readily implanted, for example, by the use of forceps, without enlarging the original lens removal incision.

In the late 1970's, techniques and equipment were developed by which a natural lens could be ultrasonically broken-up and suctioned out of the lens capsular bag which surrounds it with an irrigation solution and cannula. This improvement allowed an incision of only about 3 to 4 mm to be made. The implantation of a rigid IOL thus undesirably required enlarging the incision to accommodate the IOL.

In order to take advantage of the small incision size needed to remove the natural lens by the new, so called phacoemulsification procedure, soft deformable or foldable IOLs, initially made from an elastomeric silicone material, were soon developed. When suitably deformed by folding or rolling, these new silicone IOLs could be implanted through the small ocular incision used for the phacoemulsification procedure. After being implanted in the deformed condition, these elastic silicone IOLs would, upon release, return to their original size and condition. Since the time of introduction of the first silicone IOLs other lens materials have been utilized; these include acrylates and the like materials.

As might have been expected, new tools were needed for folding and maintaining a suitable conformation of the IOL prior to and during insertion into the area of the eye previously occupied by the natural lens. Initial efforts were understandably directed to the modification of the types of forceps used to implant rigid PMMA IOLs. However, the folding and maintaining of constant pressure on forceps prior to and during insertion proved to be awkward and difficult in some cases and various inserter or injector devices for implanting deformable IOLs have been developed which do not require the use of forceps for implantation of the IOLs. Most IOL inserter or injector devices still require the preliminary use of forceps for folding or loading the IOLs, or for holding the IOL while it is being deformed and/or for introducing the IOL or its haptics, if present, into the inserter or injector device prior to insertion. Haptics are small wire-like arms of biocompatible material which radiate out from the edge of certain IOLs and serve to hold the optic of the IOL in position inside the eye, a typical IOL comprises two haptics disposed on opposite sides of a substantially circular lens optic.

Representative examples of a few of the above-mentioned types of IOL injector or inserters are disclosed in U.S. Pat. No. 4,681,102 to Bartell; U.S. Pat. No. 4,880,000 to Holmes; U.S. Pat. No. 's 5,066,297, 4,976,716 and 4,862,885 to Cumming; and U.S. Pat. No. 's 5,494,484 and 5,582,614 to Feingold.

Virtually all, if not all, insertion devices have an elongate, slender insertion tube or nozzle at the distal end, designed to be inserted into and through the same, identically sized ocular incision made for phacoemulsification and removal of the natural lens. Proximal to this insertion tube is a region in which the IOL to be implanted is held in a pre-implant, deformed, folded or compressed condition. Proximal as used in this application indicates that portion of the inserter held by or closest to the physician and distal is used to describe that portion closest to or inside the eye.

In many inserter designs the IOL and the inserter sleeve are lubricated with a sterile, lubricous liquid, such as a viscoelastic, to ease resistance to advancing the IOL through the narrow sleeve. Typically, a slender axial shaft is provided in the handle of the insertion device for pushing the folded, rolled or otherwise deformed IOL from the holding region through the nozzle and out the distal end into the eye. The nozzle piece of the inserter is actually placed through the incision in the sclera (the tough white cover of the eye) and typically into the part of the capsular bag that remains after removal of the natural lens.

As the lens is passed through the inserter and prior to being introduced into the eye, the force applied to the inserter can become excessive to the point that the IOL is damaged. For example, the IOL can become adhered to or otherwise difficult to advance through the inserter. Applying too much force to the inserter can result in the IOL becoming damaged. Once released into the eye the optic of the IOL will return to its original shape or configuration whether damaged or not. Removal of a damaged IOL from inside the eye is awkward, time consuming and can result in unwanted surgical complications such as infection or trauma to the cornea of the eye, or the necessity to enlarge the incision in the tissue of the eye. Therefore, it is highly advantageous to avoid damaging the IOL during implantation in the eye.

Typically, the surgeon can sense the resistance to turning or pushing the handle of the inserter while advancing the IOL through the inserter and ascertain if the IOL is advancing properly through the inserter. However, the surgeon is often concerned with many other aspects of the surgery, which include looking into the eye through a microscope, giving instructions, and positioning and holding the inserter in place through the small incision. Since the procedure is performed by observing the placement of the inserter and then lens inside the eye through a microscope, the surgeon is focused on the process as it occurs within the eye, and so potentially is not fully cognizant of the resistance on the inserter handle piece.

Further, with the introduction of new IOL designs and several different types of polymeric materials of IOL construction, there are different resistances experienced when advancing different IOLs through an inserter. For example, an acrylate IOL often requires more force to move through an inserter than does a silicone IOL, and even lenses made of the same or similar materials when made by different processes and/or manufacturers differ in their degree of surface lubricity.

Therefore, it would be highly advantageous to provide a system which effectively limits the amount of force applied to an inserter to an amount which is non-damaging to the IOL.

SUMMARY OF THE INVENTION

New apparatus for inserting IOLs through an incision into an eye have been discovered. The present apparatus effectively control the amount of force applied to the apparatus, for example, to reduce, or even substantially prevent, the risk of damage to the IOL. The present apparatus are relatively straightforward, easy and inexpensive to manufacture and very effectively signal or otherwise indicate that excessive amounts of force are being used in the IOL insertion process. Using the present apparatus allows the surgeon to focus on other aspects of the surgery so as to achieve a highly beneficial result, with substantially reduced risk of damage to the IOL being inserted.

In one general aspect of the present invention, apparatus for inserting an IOL through an incision into an eye are provided and comprise a tube, an injector rod and a force transfer assembly.

The tube defines a hollow passage and has an ejection port through which the IOL is passed from the hollow passage into the eye. The injector rod is longitudinally movable within the hollow passage and has a distal portion adapted to contact the IOL within the hollow passage of the tube to urge the IOL distally through the hollow passage.

The force transfer assembly is coupled to the injector rod, is adapted to transfer sufficient force to the injector rod to effect the longitudinal movement of the injector rod, and further is adapted to prevent the transfer of sufficient force to the injector rod to effect the longitudinal movement of the injector rod in response to an increased amount of force being applied to the force transfer assembly. Thus, the force transfer assembly is adapted to allow the injector rod to move in a longitudinal direction to cause the IOL to pass through the hollow passage into the eye provided that such force is not excessive, for example, is not sufficient to cause damage to the IOL. In one very useful embodiment, the force transfer assembly provides an audible and/or tactile indication that the increased amount of force had been applied to the force transfer assembly so as to prevent the longitudinal movement of the injector rod. This embodiment can be analogized to the ratcheting action of a ratchet in that although a portion of the force transfer assembly is caused to move, for example, rotate, the longitudinal movement of the injector rod is prevented.

The amount of force required to prevent the longitudinal movement of the injector rod preferably is adjustable, for example, to take into account the differences in the level of non-damaging force that can be applied when inserting different IOLs. Thus, the present invention can be effectively employed to limit the amount of force applied to the injector rod to that amount of force which will not damage the IOL being inserted.

In one embodiment, the force transfer assembly may be considered as a combination of an actuator and a coupling/decoupling means. The coupling/decoupling means is configured for coupling the actuator to the injector rod for causing the rod to advance through the tube and push the installed IOL through the tube and out the injection port or distal end of the tube in response to the application of a normal IOL advancing force to the actuator. The coupling/decoupling means is configured for decoupling the actuator from the injector rod in response to the application of an IOL advancing force to the actuator that is substantially greater than the normal IOL advancing force; or when the installed IOL becomes stuck in the tube and an IOL advancing force substantially greater than the normal IOL advancing force is applied to the actuator. The coupling/decoupling means preferably is additionally configured for coupling the actuator to the injector rod for enabling of movement of the injector rod in the tube in an axial direction opposite to the IOL advancing direction.

In a very useful embodiment, the injector rod includes a proximal end portion having at least one radially extending projection, preferably in the form of an axially extending spline. The force transfer assembly includes a member having an inner surface defining a recess. The member is adapted to be placed on the proximal end portion of the injector rod with the projection located in the recess when the force transfer assembly is effective to transfer sufficient force to the injector rod to effect the longitudinal movement of the injector rod. An excessive amount of force applied to the force transfer assembly causes the projection to leave the recess and prevents the transfer of sufficient force to the injector rod to effect the longitudinal movement of the injector rod. The proximal end portion preferably includes a plurality of the radially extending projections and the inner surface of the cap member preferably defines a corresponding plurality of the recesses.

The projection(s) and/or the recess(es) preferably are asymmetric, in particular radially asymmetric. The projection(s) and the recess(es) are asymmetrically configured so that a given projection leaves a given recess in response to more force as the injector rod is being withdrawn from the hollow passage relative to the force needed to cause the projection to leave the recess as the injector rod is being passed into the hollow passage. This feature allows one to advantageously use more force and still effect longitudinal movement of the injector rod out of the hollow passage. To illustrate, if an IOL is being passed into the passage and becomes "stuck", that is the injector rod can not be moved longitudinally forward, that is toward the distal end of the apparatus, the force transfer assembly can be used to pass the injector rod longitudinally backwardly or proximally out of the hollow passage even though the same or greater amount of force is applied to the force transfer assembly that caused the injector rod to not be able to be moved longitudinally forward. This "greater back-out-force" feature allows the apparatus to be relatively easily unstuck, rather than being hopelessly jammed.

The injector rod preferably is adapted to be repeatedly reused, while the force transfer assembly is adapted to be disposed of after a single use. For example, the force transfer assembly or member is made of flexible or deformable polymeric material, whereas the injector rod is made of a more durable material, for example, a metal. Thus, in use, the member or force transfer assembly is placed on the injector rod and is used to cause the injector rod to move longitudinally within the hollow passage. After this use, the force transfer assembly is removed from the injector rod and disposed of. The injector rod and other reusable portions of the apparatus are sterilized or otherwise treated to be ready for reuse.

In one embodiment, the force transfer assembly includes a coupling element and a spring member effective in transferring sufficient force to the injector rod to effect the longitudinal movement of the injector rod. The spring element is adapted to be rendered ineffective, thereby preventing the transfer of sufficient force to effect the longitudinal movement of the injector rod. The coupling element and the spring member may be secured to the injector rod or to the force transfer assembly. In a very effective configuration, the apparatus preferably includes two of the coupling elements and two of the spring members.

In another embodiment, the force transfer assembly includes a cap portion adapted to be placed on the proximal end of the injector rod. The cap portion includes an inner surface which defines at least one recess into which the coupling element extends when the force from the transfer assembly is effective to transfer sufficient force to the injector rod to effect the longitudinal movement. Preferably, the inner surface defines a plurality of the recesses, each of which more preferably is asymmetric, for example, to provide the "greater back-out-force" feature described elsewhere herein. The cap portion can be secured to the injector rod. The injector rod preferably is adapted to be rotated to effect the longitudinal movement of the injector rod.

In a further embodiment, the coupling element and the spring member are secured to the force transfer assembly. For example, the injector rod may include at least one groove into which the coupling element extends when the force transfer assembly is effective to transfer sufficient force to the injector rod to effect longitudinal movement of the injector rod. The injector rod preferably includes a plurality of the grooves axially spaced apart from each other. In one embodiment, the groove or grooves are annular.

The groove or grooves preferably are asymmetrically configured so that the coupling element leaves the groove or grooves in response to more force as the injector rod is being withdrawn from the hollow passage relative to the force needed to cause the coupling element to leave the groove or grooves as the injector rod is being passed into the hollow passage.

The injector rod may include a proximal end portion configured to prevent the injector rod from decoupling from the force transfer assembly. For example, conventional clips or other fasteners may be employed to prevent the injector rod from decoupling from the force transfer assembly.

In an additional embodiment of the present invention, the force transfer assembly includes a cap element, a cap insert located with the cap element, and a cap spring member located between the cap element and the cap insert and biased to keep the cap element and the cap insert spaced apart. The cap insert includes an outwardly extending face having at least one projection or recess. The injector rod includes a proximal end face including at least one of the other of a recess or a projection. The cap member is adapted to be placed on the proximal end of the injector rod with a projection or a recess of the outwardly extending face in mating relationship with the recess or the projection of the proximal end face when the force transfer assembly is effective to transfer effective force to the injector rod to effect longitudinal movement. Preferably, the outwardly extending face and the proximal end force define a plurality of the projections or the recesses. Also, the projection(s) and/or the recess(es) of the outwardly extending face and the proximal end face are asymmetric, for example, to provide the "greater back-out-force" feature described elsewhere herein.

Each and every feature described herein, and combination of two or more of such features is included with the scope of the present invention provided that the features included in such a combination are not mutually inconsistent.

These and other aspects of the present invention are apparent in the following detained description and claims, particularly when considered in conjunction with the accompanying drawings in which like parts bare like reference numerals.

BRIEF DESCRIPTION OF THE DRAWINGS

FIG. 1 is a side perspective view, partially cut away, of an IOL insertion apparatus in accordance with the present invention.

FIG. 2 is a side plan view of the injector rod assembly removed from the body of the insertion apparatus shown in FIG. 1.

FIG. 3 is a cross-sectional view taken generally along line 3—3 of FIG. 2.

FIG. 8 is a plan view of the inner top surface of the cap member shown in FIGS. 6 and 7.

FIG. 9 is a top side view, in perspective, of the proximal end portion of the push rod assembly shown in FIGS. 6 and 7.

FIG. 10 is a top side view, in perspective, of the spring member shown in FIGS. 6 and 7.

FIG. 11 is a side plan view, partly in cross-section, of a portion of further embodiment an apparatus in accordance with the present invention.

FIG. 12 is a side plan view of a portion of the injector rod assembly shown in FIG. 11.

FIG. 13 is a cross-sectional view of a portion of an additional embodiment of an apparatus in accordance with the present invention.

DETAILED DESCRIPTION OF THE DRAWINGS

Figure 4:
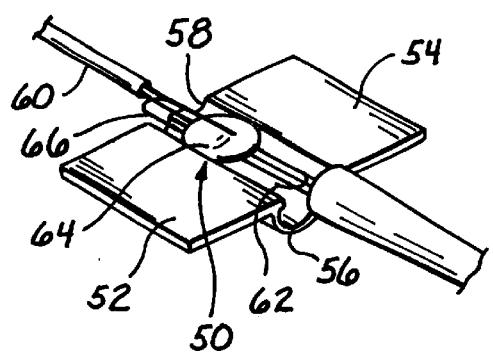
FIG. 4 is a perspective view of a folding device shown in the open position.

Referring now to FIGS. 1 to 5, IOL insertion apparatus, shown generally at 10 includes an IOL folder cartridge 12, a hollow tubular body 14, an injector rod assembly 16, and a force transfer member or actuator 18. Cartridge 12 is used to fold an IOL and to be placed in the hollow passage 20 defined by hollow body 14. Cartridge 12 includes a hollow insertion tube 21 having distal portion 22 and a distal end opening 24. In use, at least a portion of distal portion 22 is inserted through an incision in the eye so that the IOL from cartridge 12 can be passed through distal opening 24 into the eye.

The proximal end portion 26 of body 14 includes interior threads 28 which are adapted to matingly engage threads 30 on the threaded portion 32 of injector rod assembly 16.

Injector rod assembly 16 is shown in more detail in FIGS. 2 and 3. Thus, injector rod assembly 16 includes threaded portion 32, elongate tubular member 34 which is coupled to the threaded portion at coupling 33 and proximal end portion 36, which is formed integrally with the threaded portion. Tubular member 34 includes a distal tip 38 which comes in contact with the IOL in folder 12 as injector rod assembly 16 is advanced through the hollow passage 20 of body 14. This advancement is effected by rotating proximal end portion 36 to cause the entire injector rod assembly 16 to move forward or distally.

Proximal end portion 36 of injector rod assembly 16 includes a series of splines 40 which extend outwardly. In addition, splines 40 extend longitudinally along substantially the entire length of proximal end portion 36. Splines 40 are asymmetrically configured, as will be discussed hereinafter.

Injector rod assembly 16 and tubular body 14 are reusable, that is these components can be reused multiple times to insert multiple IOLs. These components preferably are made of surgical grade metal, for example, stainless steel, which can be repeatedly sterilized between uses to provide protection against cross-patient contamination. The folder cartridge 12 is disposable after a single use and is made of a suitable polymeric material. In addition, the distal tip 38 of injector rod assembly 16 maybe a polymer. The use of a polymeric or soft material for the distal tip 38 is effective to protect against damaging the IOL and useful in controlling the insertion of the IOL into the eye. If a soft polymeric material is used to produce tip 38, that portion of the push rod assembly 16 preferably is disposed of after a single use.

The force transfer member 18 is made of a polymeric material, preferably a flexible or deformable polymeric material, and includes a series of coupling/decoupling recesses 42 which correspond in number to the splines 40. Each of the recesses 42 extends longitudinally along substantially the entire length of force transfer member 18. Each of these recesses 42 is asymmetrically configured to be complimentary to the asymmetric configuration of each of the splines 40. The force transfer member 18 is positioned to cover substantially the entire outer sidewall surface 45 of proximal end portion 36. The force transfer member 18 preferably is disposed of after a single use, that is after a single IOL is inserted into an eye using apparatus 10.

Force transfer member 18 includes a number of longitudinally, outwardly extending gripping projections 44 which extend along substantially the entire length of the force transfer member. Such gripping projections 44 are effective in facilitating the manual rotation of the force transfer member 18, for example, by a surgeon using apparatus 10.

Force transfer member 18 is employed by being rotated. A certain amount of rotational force applied to the force transfer assembly 18 causes the proximal end portion 36 of injector rod assembly 16 to rotate, thus causing the injector rod assembly to move distally through hollow passage 20 of tubular body 14. This movement of injector rod assembly 16 is effected when each of the splines 40 is located in a different recess 42, as shown in FIG. 3. So long as excessive force is not applied to the force transfer member 18, the proximal end portion 36 of the injector rod assembly 16 continues to rotate in response to the rotation of the force transfer member. However, if excessive force is required to be applied to force transfer member 18 in order to cause rotation, the deformability of the force transfer member will cause the splines 40 to leave or become decoupled from the recesses 42. When this occurs, a tactile sensation, for example, a slipping sensation, is provided to the user of apparatus 10 in that it becomes much easier to rotate the force transfer assembly than when the splines 40 are located in the recesses 42. At this point, the apparatus 10 is signaling the user that excessive force has been used and that the IOL insertion process should begin again, for example, with a new IOL. This is so because the excessive force required to rotate the injector rod assembly 16 may have caused damage to the IOL in apparatus 10.

The asymmetric configurations of the splines 40 and recesses 42, as shown in FIG. 3, are such that more force is required for the splines to leave the recesses when the injector rod assembly is being passed backwardly or proximally through the hollow passage 20 of tubular body 14 relative to the amount of force required for the splines to leave the recesses if the injector rod assembly 14 is being moved distally in the hollow passage. This feature allows the user to remove the injector rod assembly 16 from the hollow passage 20 even with relatively large amounts of force. This is beneficial to allow the apparatus 10 to be reused, even though the IOL and other disposable components may need to be discarded. Put another way, without such asymmetric configuration, once excessive force has been applied and the splines 40 leave the recesses 42, it would be difficult, if not impossible, to withdraw the injector rod assembly 16 from the hollow passage 20 so that another attempt at inserting an IOL using apparatus 10 can be made. The "greater back-out force" feature described herein facilitates the reuse of the reusable components of apparatus 10 rather than having the apparatus be jammed or stuck because excessive force had to be used to move the injector rod assembly 16 distally.

Figure 5:
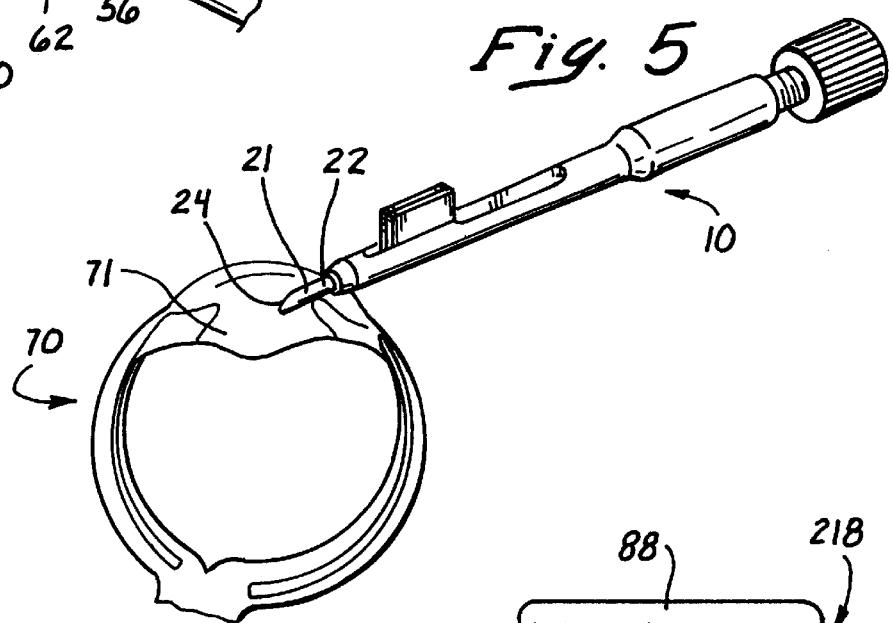
FIG. 5 is a schematic perspective drawing showing the placement of the distal portion of the insertion tube in the eye.
Figure 7:
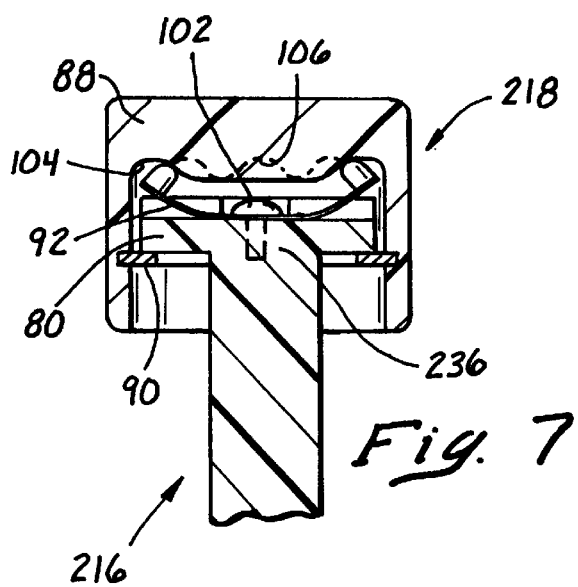
FIG. 7 is a cross-sectional view of the embodiment shown in FIG. 6.
Figure 6:
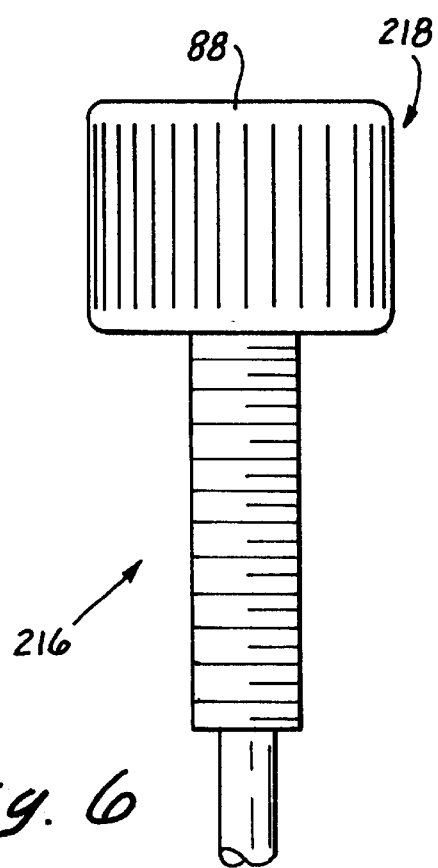
FIG. 6 is a partial side plan view of another embodiment of an apparatus in accordance with the present invention.

FIG. 4 illustrates the manner in which cartridge 12 produces the desired result of folding IOL 50. Hinge folding leaves 52 and 54 are used to open and close folding members 56 and 58, respectively. IOL 50 (in an unfolded state) is placed on folding members 56 and 58 by forceps 60. Superior haptic 62 is placed forward of optic 64, while the other haptic 66 trails the optic. Hinged folding leaves 52 and 54 are moved together, which folds the flexible, foldable optic 64 of IOL 50 in half. After IOL 50 is folded, the forceps 60 is removed. The closed loading cartridge 12, containing the folded IOL 50, is then loaded into tubular body 14 of apparatus 10, through opening 19. Insertion apparatus 10 is operated and functions as follows. When it is desired to insert IOL 50 into an eye, the apparatus 10 and IOL are placed in a configuration as shown in FIG. 1. Referring now to FIG. 5, the IOL is to be placed in the eye 70 into an area formerly occupied by the natural lens of the eye. With the IOL in its folded position within apparatus 10, the distal portion 22 of insertion tube 21 is ready for insertion through an incision in the sclera of eye 70. Capsular bag 72 protects the posterior segment of the eye 70. With the distal portion 22 inserted within the eye 70 and the distal end opening 24 positioned so that the IOL can unfold into the location within the eye 70 best suited for permanent implantation, the user rotates force transfer member 18 to advance the injector rod assembly 16 distally. The injector rod assembly 16 is advanced distally, which in turn moves the IOL distally into insertion tube 21. As long as no excessive force is required to be applied to force transfer member 18 to maintain the rotation of the injector rod assembly 16, no indication is given that the IOL 50 is possibly damaged by such excessive force. The IOL emerges from the distal end opening 24 and is positioned in the eye with reduced risk that the IOL itself has been damaged.

FIG. 5 shows the eye 70 having an incision in the sclera through which the distal portion 22 is passed. Alternately, the incision can be made through the cornea. Distal portion 22 has a sufficiently small cross-section to pass into the eye 70 through a 3.0 mm incision in the sclera. Folding leaves 52 and 54, in contact with each other when lens folding cartridge 12 is in the closed position, can be grasped by an operator and used to guide and position distal portion tube into its desired position within the eye.

After the IOL has been inserted in eye 70, distal portion 22 is removed from the eye. If needed, the IOL can be repositioned in the eye by a small, bent needle or similar tool inserted into the same incision.

Once the IOL is properly positioned in eye 70 and apparatus 10 is withdrawn from the eye, the incision in the sclera can be closed, for example, using conventional techniques. After use, cartridge 12 and force transfer member 18 preferably are disposed of. Remaining portions of apparatus 10, as described above, can be reused after sterilization.

FIGS. 6 to 10 illustrate another embodiment of the present invention. Except as expressly described herein, this other insertion apparatus, identified generally as 210, includes the same components and is structured and functions similarly to the insertion apparatus 10. Components of the other apparatus 210 corresponding to components of the apparatus 10 are identified by the same reference numerals increased by 200.

The primary differences between the apparatus 210 and apparatus 10 relate to the force transfer member or assembly and the proximal end of the injector rod assembly. Specifically, the force transfer member 18 is replaced by force transfer assembly, shown generally at 218, and described in detail hereinafter. Also, the proximal end portion of the injector rod assembly 216 has an enlarged flattened head 80 including groves 82 and 84 which cross each other centrally. At the center of the flattened head 80 is a fastener hole 86.

Force transfer assembly 218 includes a cap 88 which is secured to the injector rod assembly 216 by a clip 90 which is coupled to the cap and extends inwardly to entrap flattened head 80.

A spring element 92 (FIG. 10) is provided including two generally flat and opposing legs 94 and two generally upwardly extending and opposing legs 96. A contact pin 98 is secured, for example, welded, to each of the upwardly extending legs 96, as shown in FIG. 10. A fastener hole 100 is located through the center of spring element 92. Spring element 92 is fitted to the flattened head 80 using fastener 102. In this manner, the flat legs 94 extend into grove 82 and upwardly extending legs 96 are placed at least partially in groves 84.

The inner top surface 104 of cap 88 includes a series of asymmetric recesses 106.

Force transfer assembly 218 functions as follows. The cap 88 and spring member 92 are positioned so that the pins 98 fit in two of the recesses 106. As long as no excessive force is placed on the force transfer assembly 218, and in particular on cap 88, the rotation of cap 88 results in the rotation of flattened head 80 and the entire injector rod assembly 216. In this manner, the injector rod assembly 216 can be advanced through the hollow passage of the hollow tubular body of apparatus 210, in a manner substantially similar to the functioning of apparatus 10 discussed above, to insert an IOL into an eye.

If excessive force is applied to cap 88, the pins 98 leave the recesses 106 so that no further rotation of the injector assembly 116 occurs even though the cap continues to be rotated. The recesses 106 are asymmetrically configured so that more force is required before the pins 98 leave the recesses 106 when the cap member 88 is being rotated to withdraw the injector rod assembly 216 from the hollow space of the hollow tube. Thus, as discussed above with regard to apparatus 10, apparatus 210 can be reset rather than being stuck in a situation where the injector rod assembly 216 does not rotate either in or out of the hollow passage of this tubular body.

FIGS. 11 and 12 illustrate a further embodiment of the present invention unless. Except as expressly described herein, this further insertion apparatus identified generally as 310, includes the same components and is structured and functions similarly to apparatus 10. Components of the further apparatus 310 corresponding to components of apparatus 10 are indicated by the same reference number increased by 300.

The primary differences between further apparatus 310 and apparatus 10 relate to the structure of the force transfer assembly and the proximal end portion of the injector rod assembly.

The force transfer assembly 318 includes a grip element 111 which defines a thumb hole 113. In addition, force transfer assembly 318 includes a centrally located bore 115 in which the proximal end portion 117 of injector rod assembly 316 is located. A spring 119 is situated in a side bore 121 located in the lower sidewall 123 of force transfer assembly 318. A pin 125 is affixed to the spring 119 and extends into the opening 115.

As shown in FIG. 12, the proximal end portion 117 of the injector rod assembly 316 includes a series of annular grooves 131. The proximal end member 133 of injector rod assembly 316 has a somewhat larger cross-sectional area than the largest portion of the groves 131.

Apparatus 310 functions as follows. The proximal end portion of injector assembly 316 is placed in the hole 115 of force transfer assembly 318, the spring 119 element is placed so that the pin 125 extends into one of the grooves 131. With this configuration, force transfer assembly 318 is directly pushed in or pulled out (rather than being rotated as with forced transfer assembly 118) to provide for forward or distal movement of injector rod assembly 316 in the hollow passage of the tubular body of apparatus 310 or the withdrawal of injector rod assembly 316 from the hollow passage of the tubular body of apparatus 310. As long as no excessive force is applied to force transfer assembly 318, the pin 125 remains in groove 131 and the injector rod assembly moves directly with the force transfer assembly 318. However, if excessive force is applied to force transfer assembly 318, the pin 125 leads leaves grooves 131. This causes a slippage which is easily recognized, for example, by the user of the apparatus 310. This slippage is an indication that excessive force has been applied and that the IOL being inserted may have been damaged.

The grooves 131 are asymmetrically configured so that less force is required to have the pin 125 leave the grooves as the injector rod assembly 316 is being moved forward into the apparatus 310 relative to the amount of force required for the pin to leave the grove when the injector rod assembly is being withdrawn from the apparatus 310. As before, this feature is effective to avoid the apparatus 310 from being permanently stuck.

In addition, the enlarged proximal end member 133 is structured to be sufficiently large so that the pin 125 does not allow member 133 to leave the bore 115. Thus, member 133 is effective in coupling the injector rod assembly 316 to the force transfer assembly 318.

FIG. 13 illustrates yet another embodiment of the present invention. Except as expressly described herein, this additional apparatus, identified generally as 410, includes the same components and is structured and functions similarly to apparatus 10. Components of the additional apparatus 410 which correspond to components of apparatus 10 are identified by the same reference number increased by 400.

The primary differences between apparatus 410 and apparatus 10 have to do with the structure of the force transfer assembly 418 and the structure of the proximal end portion of the injector rod assembly 416. Specifically, force transfer assembly 418 includes a cap member 141 including an inner surface 143 to which is secured spring member 145. In addition, spring member 145 is coupled to cap insert 147 which includes a series of recesses 149.

The proximal end 151 of injector rod assembly 416 is relatively enlarged and includes a proximal surface 153 including a series of projections 155. The projections 155 are adapted to mate or fit into recesses 149. Cap member 141 is secured to the proximal end 151 of injector rod assembly 416 using a clip 157 which is coupled to the cap member and extends upwardly to entrap the enlarged proximal end. The projections 149 and recesses 155 are asymmetrical configured so that more force is required to remove the projections from the recesses as cap member 141 is being rotated to withdraw the injector rod assembly 416 from apparatus 410 relative to the force required to remove the projections from the recesses as the cap member is being moved distally into the apparatus 410 the eye.

Force transfer assembly 418 functions as follows. When it is desired to insert an IOL into an eye, cap member 141 is rotated so as to advance injector rod assembly 416 forward toward to eye. So long as no excessive force is applied to cap member 141, the projections 155 remain in the recesses 149. However, if excessive force is applied to cap member 141, the projections 149 leave the recesses 155 and result in push rod assembly 416 not being advanced even though the cap member 141 continues to be rotated. At this point, this situation is tactually signaled and possibly even audibly signaled to the user of apparatus 410. In this instance, the rotation of the cap member is reversed to withdraw the injector rod assembly 416 so that the IOL can be inspected to determine if any damage has occurred.

While this invention has been described with respect to various specific examples and embodiments, it is to be understood that the invention is not limited thereto and that it can be variously practiced within the scope of the following claims.

What is claimed is:

1. An apparatus for controlling longitudinal movement of a longitudinally movable injector rod in a hollow passage in a hollow tubular body, said apparatus comprising:
   a longitudinally movable injector rod adapted to move an intraocular lens in a hollow passage in a hollow tubular body; and
   a force transfer assembly coupled to the injector rod, adapted to transfer sufficient force to the injector rod to effect longitudinal movement of the injector rod and an intraocular lens in a hollow passage in a hollow tubular body, and further adapted to decouple from the infector rod and to prevent the transfer of sufficient force to the injector rod to effect longitudinal movement of the injector rod and an intraocular lens in a hollow passage in a hollow tubular body in response to an increased force, relative to the sufficient force, being applied to the force transfer assembly seeking to effect longitudinal movement of the injector rod and an intraocular lens in a hollow passage in a hollow tubular body.

2. The apparatus of claim 1 wherein the injector rod includes a proximal end region including at least one radially extending projection, and the force transfer assembly includes a member having an inner surface defining a recess, the member being adapted to be removably placed on the proximal end region with the at least one radially extending projection located in the recess when the force transfer assembly is effective to transfer sufficient force to the injector rod to effect longitudinal movement of the injector rod and an intraocular lens in a hollow passage in a hollow tubular body and to be decoupled from the proximal end region in response to the increased force being applied to the force transfer assembly.

3. The apparatus of claim 2 wherein the proximal end region includes a plurality of the radially extending projections and the inner surface defines a corresponding plurality of the recesses.

4. The apparatus of claim 2 wherein the member is adapted to be disposed of after a single use.

5. The apparatus of claim 2 wherein the member is made of a deformable polymeric material.

6. The apparatus of claim 2 wherein the force transfer assembly is adapted to be rotated to effect longitudinal movement of the injector rod in a hollow passage in a hollow tubular body.

7. The apparatus of claim 1 wherein the force transfer assembly includes a coupling element and a spring member adapted to be effective in transferring sufficient force to the injector rod to effect longitudinal movement of the injector rod and an intraocular lens in a hollow passage in a hollow tubular body, the spring member being adapted to be rendered ineffective to prevent the transfer of sufficient force to effect longitudinal movement of the injector rod and an intraocular lens in a hollow passage in a hollow tubular body.

8. The apparatus of claim 7 wherein the coupling element and the spring member are adapted to be secured to the injector rod.

9. The apparatus of claim 7 wherein the injector rod includes at least one groove, and the coupling element is adapted to extend into the at least one groove when the force transfer assembly is effective to transfer sufficient force to the injector rod to effect longitudinal movement of the injector rod and an intraocular lens in a hollow passage of a hollow tubular body.

10. The apparatus of claim 9 wherein the coupling element is adapted to leave the groove in response to more force as the injector rod is being withdrawn from the hollow passage relative to the force needed to cause the coupling element to leave the groove as the injector rod is being passed in a hollow passage of a hollow tubular body.

11. An apparatus for controlling longitudinal movement of a longitudinally movable injector rod in a hollow passage in a hollow tubular body, said apparatus comprising:
   a longitudinally movable injector rod adapted to move an intraocular lens in a hollow passage in a hollow tubular body; and
   a force transfer assembly coupled to the injector rod, adapted to transfer sufficient force to the injector rod to effect longitudinal movement of the injector rod and an intraocular lens in a hollow passage in a hollow tubular body, and further adapted to decouple from the injector rod in response to an increased force, relative to the sufficient force, being applied to the force transfer assembly seeking to effect longitudinal movement of the injector rod and an intraocular lens in a hollow passage in a hollow tubular body.

12. The apparatus of claim 11 wherein the force transfer assembly includes a coupling element and a spring member adapted to be effective in transferring sufficient force to the injector rod.

13. The apparatus of claim 12 wherein the injector rod includes at least one groove, and the coupling element is adapted to extend into the at least one groove when the force transfer assembly is effective to transfer sufficient force to the injector rod to effect longitudinal movement of the injector rod in a hollow passage in a hollow tubular body.

14. An apparatus for controlling longitudinal movement of a longitudinally movable injector rod in a hollow passage in a hollow tubular body, said apparatus comprising:
   a longitudinally movable injector rod adapted to move in a hollow passage in a hollow tubular body, the injector rod includes a proximal end region including at least one radially extending projection; and
   a force transfer assembly coupled to the injector rod, adapted to transfer sufficient force to the injector rod to effect longitudinal movement of the injector rod in a hollow passage in a hollow tubular body, and further adapted to prevent the transfer of sufficient force to the injector rod to effect longitudinal movement of the injector rod in a hollow passage in a hollow tubular body in response to an increased amount of force being applied to the force transfer assembly, the force transfer assembly includes a member having an inner surface defining a recess, the member being adapted to be placed on the proximal end region with the at least one radially extending projection located in the recess when the force transfer assembly is effective to transfer sufficient force to the injector rod to effect longitudinal movement of the injector rod in a hollow passage in a hollow tubular body, the recess is asymmetrically configured so that the projection leaves the recess in response to more force as the injector rod is being withdrawn from a hollow passage in a hollow tubular body relative to the force needed to cause the projection to leave the recess as the injector rod is being passed in a hollow passage in a hollow tubular body.

15. An apparatus for controlling longitudinal movement of a longitudinally movable injector rod in a hollow passage in a hollow tubular body, said apparatus comprising:
   a longitudinally movable injector rod adapted to move in a hollow passage in a hollow tubular body; and
   a force transfer assembly coupled to the injector rod, adapted to transfer sufficient force to the injector rod to effect longitudinal movement of the injector rod in a hollow passage in a hollow tubular body, and further adapted to prevent the transfer of sufficient force to the injector rod to effect longitudinal movement of the injector rod in a hollow passage in a hollow tubular body in response to an increased amount of force being applied to the force transfer assembly, the force transfer assembly includes a coupling element and a spring member adapted to be secured to the injector rod and to be effective in transferring sufficient force to the injector rod to effect longitudinal movement of the injector rod in a hollow passage in a hollow tubular body, the spring member being adapted to be rendered ineffective to prevent the transfer of sufficient force to effect longitudinal movement of the injector rod in a hollow passage in a hollow tubular body, the force transfer assembly further includes a cap portion adapted to be placed on a proximal end of the injector rod, the cap portion including an inner surface defining at least one recess into which the coupling element extends when the force from the transfer assembly is effective to transfer sufficient force to the injector rod to effect longitudinal movement of the injector rod in a hollow passage in a hollow tubular body.

16. The apparatus of claim 15 wherein the inner surface defines a plurality of the recesses.

17. The apparatus of claim 16 wherein the recesses are asymmetric.

18. An apparatus for controlling longitudinal movement of a longitudinally movable injector rod in a hollow passage in a hollow tubular body, said apparatus comprising:
   a longitudinally movable injector rod adapted to move in a hollow passage in a hollow tubular body; and
   a force transfer assembly coupled to the injector rod, adapted to transfer sufficient force to the injector rod to effect longitudinal movement of the injector rod in a hollow passage in a hollow tubular body, and further adapted to prevent the transfer of sufficient force to the injector rod to effect longitudinal movement of the injector rod in a hollow passage in a hollow tubular body in response to an increased amount of force being applied to the force transfer assembly, the force transfer assembly includes a cap element, a cap insert located within the cap element and a cap spring member located between the cap element and the cap insert and biased to keep the cap element and the cap insert spaced apart, the cap insert including an outwardly extending face having at least one projection or recess, and the injector rod includes a proximal end face including at least one of the other of a recess or a projection, the cap member being adapted to be placed on the proximal end of the injector rod with the projection or the recess of the outwardly extending face in mating relationship which the recess or the projection of the proximal end face when the force transfer assembly is effective to transfer sufficient force to the injector rod to effect longitudinal movement of the injector rod in a hollow passage in a hollow tubular body.

19. The apparatus of claim 18 wherein the outwardly extending face defines a plurality of the projections or the recesses.

20. The apparatus of claim 18 wherein the at least one projection or the at least one recess is asymmetrically configured.

* * * * *